(12) United States Patent
Negiz et al.

(10) Patent No.: US 7,615,197 B2
(45) Date of Patent: *Nov. 10, 2009

(54) PROCESSES FOR PRODUCING XYLENES USING ISOMERIZATION AND TRANSALKYLATION REACTIONS AND APPARATUS THEREFOR

(75) Inventors: Antoine Negiz, Wilmette, IL (US); James E. Rekoske, Glenview, IL (US); Edwin P. Boldingh, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 133 days.

This patent is subject to a terminal disclaimer.

(21) Appl. No.: 11/945,617

(22) Filed: Nov. 27, 2007

(65) Prior Publication Data

US 2008/0067053 A1    Mar. 20, 2008

Related U.S. Application Data

(63) Continuation of application No. 11/343,372, filed on Jan. 31, 2006, now Pat. No. 7,314,601.

(51) Int. Cl.
*B01J 10/00* (2006.01)
*C07C 6/12* (2006.01)

(52) U.S. Cl. .............. 422/193; 422/195; 422/194; 422/149; 585/470; 585/477

(58) Field of Classification Search ............... 422/193, 422/195, 194, 149; 585/470, 477
See application file for complete search history.

(56) References Cited

U.S. PATENT DOCUMENTS

| | | | |
|---|---|---|---|
| 4,341,914 A | 7/1982 | Berger | 585/474 |
| 4,642,406 A | 2/1987 | Schmidt | 585/477 |
| 6,512,154 B1 | 1/2003 | Magne-Drisch et al. | 585/470 |
| 6,740,788 B1 | 5/2004 | Maher et al. | 585/319 |
| 6,774,273 B2 | 8/2004 | Xie et al. | 585/304 |
| 6,867,339 B2 | 3/2005 | Kong et al. | 585/319 |
| 2004/0186332 A1 | 9/2004 | Kong et al. | 585/475 |

OTHER PUBLICATIONS

Robert A. Meyers, *Handbook of Petroleum Refining Processes*, 2d. Edition, 1997, pp. 2.1-2.62.

*Primary Examiner*—Thuan Dinh Dang
(74) *Attorney, Agent, or Firm*—Maryann Maas

(57) ABSTRACT

Processes for making xylene isomer using integrated transalkylation and isomerization reaction zones to enhance xylene recovery and enable reduction in capital costs and energy consumption.

6 Claims, 4 Drawing Sheets

PROCESSES FOR PRODUCING XYLENES USING ISOMERIZATION AND TRANSALKYLATION REACTIONS AND APPARATUS THEREFOR

CROSS REFERENCE TO RELATED APPLICATION

This application is a Continuation of copending application Ser. No. 11/343,372 filed Jan. 31, 2006, the contents of which are hereby incorporated by reference in its entirety.

FIELD OF THE INVENTION

This invention pertains to processes for producing xylenes from feed streams containing aromatics and non-aromatics and apparatus useful in such processes.

BACKGROUND OF THE INVENTION

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene which is difficult to separate or to convert. Para-xylene in particular is a major chemical intermediate. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture which approaches equilibrium concentrations.

In general, a xylene production facility can have various types of processing reactions. One is a transalkylation in which benzene and/or toluene are reacted with $C_9+$ aromatics to form more methylated aromatics. Another is xylene isomerization, which may also include ethylbenzene conversion, where a non-equilibrium mixture of xylenes is isomerized. The ethylbenzene may be isomerized to xylenes or may be dealkylated to yield, e.g., benzene. And another is disproportionation in which toluene is disproportionated. The disproportionation reaction yields one mole of benzene per mole of xylene produced.

The production of xylenes is practiced commercially in large-scale facilities and is highly competitive. Concerns exist not only about the effective conversion of feedstock to product xylenes, but also other competitive aspects with respect to such facilities including capital costs and energy costs. A prior art aromatics complex flow scheme has been disclosed by Meyers in part 2 of the Handbook of Petroleum Refining Processes, 2d. Edition, in 1997 published by McGraw-Hill.

In addition to improvements in catalysts for various of the reactions that may be used in the process such as isomerization, transalkylation and disproportionation, efforts have been expended to develop process flow schemes for at least one of reducing operating costs, improving conversion of the feedstock to sought product or reducing capital costs.

U.S. Pat. No. 4,341,914 to Berger discloses a transalkylation process with recycle of $C_{10}$ alkylaromatics in order to increase yield of xylenes from the process. The transalkylation process is also preferably integrated with a para-xylene separation zone and a xylene isomerization zone operated as a continuous loop receiving mixed xylenes form the transalkylation zone feedstock and effluent fractionation zones. See also, U.S. Pat. No. 6,512,154.

U.S. Pat. No. 6,740,788 to Mahar, et al., discloses a process in which the feed to a transalkylation reactor is fractionated in a benzene column prior to being passed to the reactor.

U.S. Pat. No. 6,774,273 to Xie, et al., discloses a process for producing xylenes containing a transalkylation section, a disproportionation section and an isomerization section.

U.S. Pat. No. 6,867,339 of Kong, et al., discloses a process for producing xylenes containing a transalkylation section, a disproportionation section and an isomerization section.

US 2004/0186332 of Kong, et al., discloses a process for producing xylenes using a disproportionation and transalkylation of toluene and heavy aromatics.

Still a need exists to improve the economics of xylene production facilities.

SUMMARY OF THE INVENTION

In accordance with this invention, improved processes for making xylenes can be provided by integrating the transalkylation and xylene isomerization sections of a xylene production facility. In its broad aspect, integration is achieved by processing reaction effluents from each section in a common distillation assembly to recover xylenes as well as remove toluene and benzene from the xylene. In more preferred aspects of the processes and apparatus of the invention, transalkylation and isomerization are conducted in a common reactor containing one or more reaction zones. Hence further economic benefits can be achieved. In preferred aspects of the invention, the transalkylation and isomerization are conducted under substantially the same conditions of pressure and temperature, thus further simplifying the processes.

Another beneficial application of the processes of this invention is for retrofitting existing xylene isomer production facilities that employ no transalkylation unit operation by modifying an existing xylene isomerization unit operation to effect both xylene isomerization and transalkylation of heavier alkylaromatics. The retrofitting may involve a replacement of the isomerization reactor, and in some instances, can be effected using the same reactor but using either different catalyst zones or a catalyst capable of effecting both transalkylation and isomerization. Advantageously, little, if any, modification would be required to the existing fractionation operations.

In one broad aspect of the invention, continuous processes for enhancing xylene content of aromatic hydrocarbon-containing feed comprise:

a. subjecting at least one of benzene and toluene ("Light Aromatic") and at least one heavier alkylaromatic ("Heavier Aromatic" having 9 and or 10 carbon atoms), said Heavier Aromatic being derived from a fractionation of an aromatic hydrocarbon-containing stream containing Heavier Aromatic and at least one lighter or heavier aromatic hydrocarbon, to transalkylation conditions, said conditions including catalyst capable of transalkylating Light Aromatic and Heavier Aromatic to xylene, to provide transalkylation product containing xylene, toluene, and benzene;

b. subjecting non-equilibrium mixture containing at least one xylene isomer to isomerization conditions, said isomerization conditions including catalyst capable of isomerizing xylene, to provide an isomerized product containing a redistributed mixture of xylene isomers; and c. separating, preferably by fractionation, an admixture of at least a portion of the transalkylation product and at least a portion of the isomerized product to provide a xylene fraction depleted in Light Aromatic.

The admixture may be formed prior to step (c) or during step (c). Where before step (c), the admixing may be effected:
  (i) by mixing the products from steps (a) and (b) or
  (ii) by introducing at least a portion of the transalkylation product of step (a) into step (b) or
  (iii) by introducing at least a portion of isomerized product of step (b) into step (a) or
  (iv) by simultaneously conducting steps (a) and (b) under conditions that are isomerization conditions and transalkylation conditions.

Step (c) may be effected in one or more distillation columns, including flash fractionation columns, and preferably provides (i) a benzene-containing fraction depleted in xylenes and toluene, (ii) a toluene fraction depleted in xylenes, and (iii) a xylene fraction depleted in toluene and benzene.

In a preferred aspect of the processes of the invention, at least an aliquot portion of the transalkylation product of step (a) is subjected to the isomerization conditions of step (b). In one preferred embodiment of this aspect of the invention, at least a portion of the non-equilibrium mixture is introduced into transalkylation step (a) and can thus pass with the transalkylation product into the isomerization of step (b). Hence, the transalkylation and isomerization reaction zones may in flow series. In yet a further preferred aspect, the transalkylation and isomerization may be conducted in a single vessel with zones for each of the transalkylation and isomerization reactions.

In another preferred embodiment of the broad aspects of the invention, the transalkylation catalyst and the isomerization catalyst are the same and transalkylation and isomerization may occur within a single reaction zone. If desired, at least a portion of the non-equilibrium mixture of xylenes can be introduced with the Light Aromatic and Heavier Aromatic. If desired, at least a portion of the non-equilibrium mixture is introduced into the reaction zone subsequent to the point of introduction of the Light Aromatic and Heavier Aromatic.

In yet another preferred embodiment of the broad aspects of this invention, at least a portion of the non-equilibrium mixture of xylenes is introduced into the isomerization step (b).

In preferred aspects of the processes of this invention, the transalkylation conditions and isomerization conditions are substantially the same. Thus, the use of a single reactor to effect both transalkylation and isomerization is facilitated regardless of whether the catalysts are the same or different.

In a further preferred embodiment of the processes of this invention, the non-equilibrium mixture of xylenes contains ethylbenzene. The isomerization conditions may also catalytically convert the ethylbenzene, e.g., by isomerization to xylenes or, more preferably, by dealkylation of ethylbenzene.

Another broad aspect of this invention pertains to continuous processes for producing para-xylene comprising:
  a. separating by fractionation a feed comprising xylenes and Heavier Aromatic to provide a lower boiling fraction containing at least two xylene isomers, one of which is para-xylene and a higher boiling fraction containing Heavier Aromatic;
  b. selectively separating para-xylene isomer from the lower boiling fraction of step (a) to provide a para-xylene isomer fraction and a non-equilibrium xylene isomer fraction;
  c. subjecting at least a portion of the higher boiling fraction containing Heavier Aromatic from step (a) to transalkylation conditions, said conditions including the presence of Light Aromatic and catalyst capable of transalkylating Light Aromatic and Heavier Aromatic to xylene, to provide transalkylation product containing xylene, benzene and toluene;
  d. subjecting at least a portion of the non-equilibrium mixture containing at least one xylene isomer of step (b) to isomerization conditions, said isomerization conditions including catalyst capable of isomerizing xylene, to provide an isomerate containing xylenes;
  e. separating, preferably by fractionation, an admixture of at least a portion of the transalkylation product and at least a portion of the isomerized product to provide a xylene fraction depleted in Light Aromatic; and
  f. passing at least a portion of the xylene fraction from step (e) to step (a).

Preferably the separation of step (e) provides (i) a benzene-containing fraction depleted in xylenes and toluene, (ii) a toluene fraction depleted in xylenes, and (iii) a xylene fraction depleted in toluene and benzene and at least a portion of the toluene fraction from step (e) is passed to step (c).

Often the higher boiling fraction from step (a) contains hydrocarbons of greater than 10 carbon atoms. Thus in a preferred embodiment, this higher boiling fraction is subjected to fractionation to provide a lower boiling fraction containing Heavier Aromatic and a higher boiling fraction containing hydrocarbons of greater than 10 carbon atoms, and at least a portion of the lower boiling fraction is the higher boiling fraction containing Heavier Aromatic for step (c).

In its broad aspect, the apparatus of this invention comprise:
  a. a toluene distillation assembly having a feed inlet, a first outlet adapted to receive a toluene-containing fraction and a second outlet below said first outlet adapted to receive a xylene-containing fraction;
  b. a xylene distillation assembly having a feed inlet in fluid communication with the second outlet of the toluene distillation assembly, said xylene distillation assembly having a first outlet adapted to receive a para-xylene-containing fraction and a second outlet below said first outlet adapted to receive a Heavier Aromatic-containing fraction;
  c. a selective xylene isomer separation assembly having a feed inlet in fluid communication with the first outlet of the xylene distillation assembly, a product outlet adapted to receive selectively separated xylene isomer, and a reject outlet adapted to receive a non-equilibrium mixture of xylene isomers;
  d. at least one reactor having a feed inlet, a feed outlet and therebetween at least one catalyst-containing zone, at least one of said reactors contains catalyst adapted for transalkylation and at least one of said reactors contains catalyst adapted for xylene isomerization, in which the first outlet of the toluene distillation assembly and the second outlet of the xylene distillation assembly are in fluid communication with the at least one reactor containing catalyst adapted for transalkylation and in which the reject outlet of the selective xylene isomer separation assembly is in fluid communication with the at least one reactor containing catalyst adapted for xylene isomerization; and e. a stripper distillation assembly having an inlet in fluid communication with the feed outlet of the at least one reactor containing catalyst adapted for transalkylation and with the feed outlet of the at least one reactor containing catalyst for xylene isomerization, said stripper distillation assembly having a first outlet adapted to provide a toluene-containing fraction which outlet is in fluid communication with the toluene distillation assembly.

In the preferred apparatus of this invention, one reactor contains catalyst for transalkylation and catalyst for xylene isomerization.

DETAILED DESCRIPTION OF THE INVENTION

Figure 2:
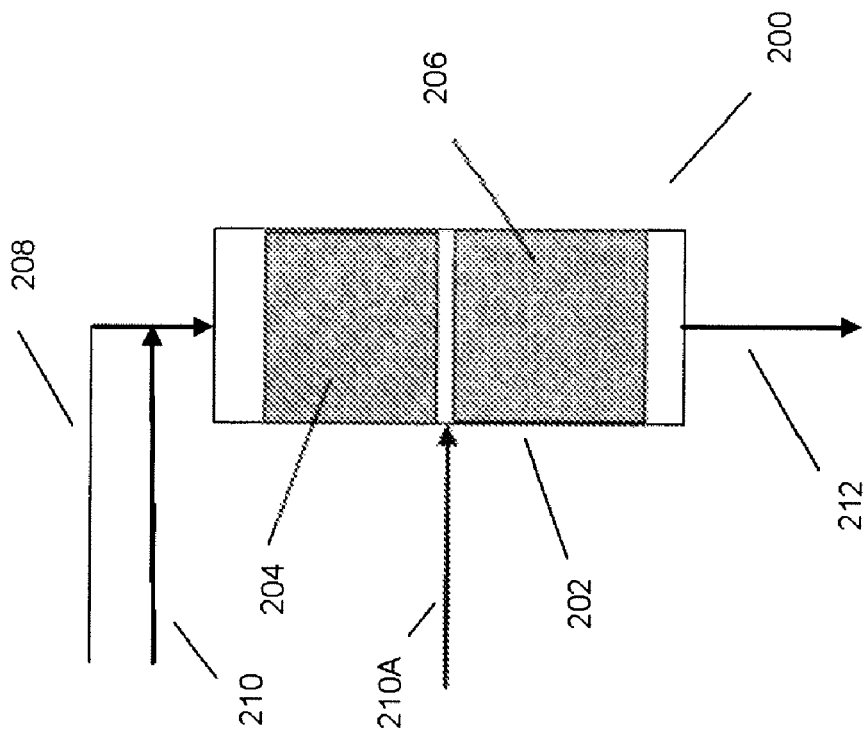
FIG. 2 is a schematic representation of a reactor system having a single reactor vessel having two zones therein for practicing processes in accordance with this invention.

Processes for the production of xylene isomer are disclosed, for instance, in Robert A. Meyers, Handbook of Petroleum Refining Processes, Second Edition, McGraw-Hill, 1997, Part 2.

In general, the feed stream for aromatics isomerization is typically a $C_8$ aromatics stream from which one or more xylenes have been removed as product. The $C_8$ aromatics stream from which one or more xylenes are removed is typically derived from xylene containing recycle and fresh $C_8$ aromatics feed. Usually the fresh $C_8$ aromatics feed is obtained from processes, such as catalytic reforming and/or extraction, for the production and recovery of aromatics from other hydrocarbons. Hence, fresh alkylaromatic for use in the present invention may be found in appropriate fractions from various refinery petroleum streams, e.g., as individual components or as certain boiling-range fractions obtained by the selective fractionation and distillation of catalytically cracked or reformed hydrocarbons. Concentration of the $C_8$ aromatics in these streams is optional; the process of the present invention allows the isomerization of alkylaromatic-containing streams such as catalytic reformate with or without subsequent aromatics extraction to remove non-aromatics.

Most commercial facilities recover from a $C_8$ aromatics stream at least para-xylene, and sometimes also ortho-xylene, as products and isomerize the remaining $C_8$ aromatics to recover more of the para-xylene, and ortho-xylene if applicable. Hence, the feed stocks to the aromatics isomerization process of this invention comprise non-equilibrium xylene and, most frequently, ethylbenzene. These aromatic compounds are in a non-equilibrium mixture, i.e., at least one $C_8$ aromatic isomer is present in a concentration that differs substantially from the equilibrium concentration at isomerization conditions. Thus, a non-equilibrium xylene composition exists where one or two of the xylene isomers are in less than equilibrium proportion with respect to the other xylene isomer or isomers. The xylene in less than equilibrium proportion may be any of the para-, meta- and ortho-isomers. As the demand for para- and ortho-xylenes is greater than that for meta-xylene, usually, the feed stocks will contain meta-xylene. Generally the mixture will have an ethylbenzene content of about 1 to about 60 mass-percent, an ortho-xylene content of 0 to about 35 mass-percent, a meta-xylene content of about 20 to about 95 mass-percent and a para-xylene content of 0 to about 30 mass-percent. Usually the non-equilibrium mixture is prepared by removal of para-, ortho- and/or meta-xylene from a fresh $C_8$ aromatic mixture obtained from an aromatics-production process. Particularly preferred processes of this invention provide for the selective recovery of each of para-xylene and ortho-xylene. The feed stocks may contain other components, including, but not limited to naphthenes and acyclic paraffins, as well as higher and lower molecular weight aromatics.

The invention will be further described with reference to the drawings which are not to be construed as being in limitation of the broad aspects of the invention.

As stated above, the feedstock for producing xylene isomer can vary widely but is usually derived from a refinery stream. In such situations, the feedstock, which has had sulfur removed, often has a composition within the ranges set forth in Table 1. If desired, olefins may also be removed. The feedstock may additionally contain aromatics having 11, 12, or greater carbon atoms, and these additional aromatics may also undergo transalkylation in the process of this invention.

TABLE 1

| Component | Typical Range, mass-% | More Frequent Range, mass-% |
| --- | --- | --- |
| Aliphatics, $C_6$ and lower | 0-20 | 2-15 |
| Aliphatics, $C_7$ and $C_8$ | 3-12 | 3-10 |
| Aliphatics, above $C_8$ | 0-5 | 0-2 |
| Benzene | 1-20 | 1-10 |
| Toluene | 10-40 | 15-30 |
| $C_8$ aromatics | 10-50 | 25-40 |
| $C_9$ aromatics | 0-20 | 10-15 |
| $C_{10}$ and above aromatics | 0-10 | 1-7 |

This feed is typically fractionated in a deheptanizer distillation column to provide a lower boiling stream containing toluene and lighter components and a higher boiling fraction containing xylenes and heavier components.

Figure 3:
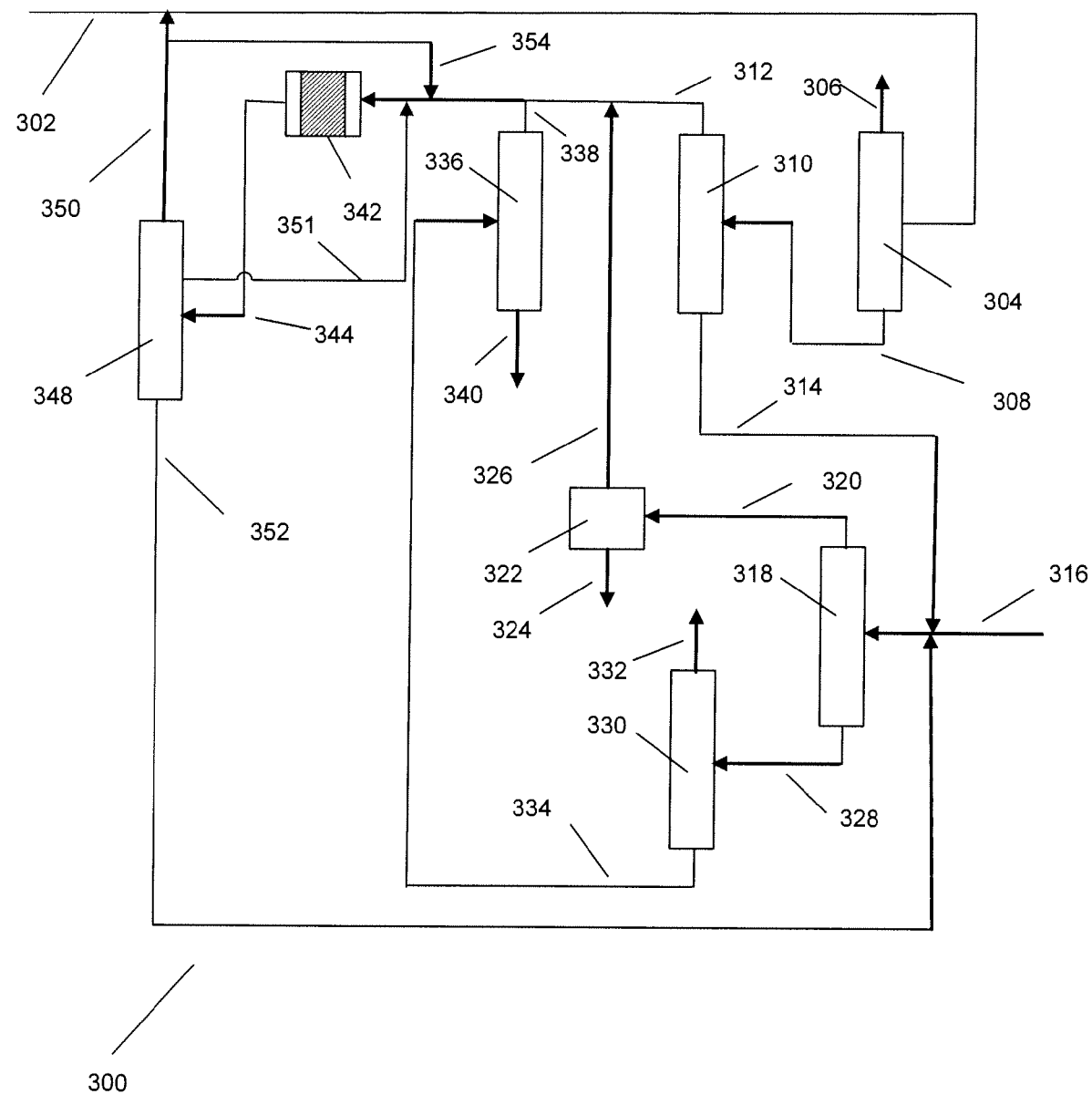
FIG. 3 is a schematic representation of a xylene isomer production apparatus in accordance with this invention.

With reference to FIG. 3, a para-xylene and ortho-xylene production facility, generally designated as 300, obtains a xylene-containing feed that also contains toluene and lighter hydrocarbons via line 302. If desired, this stream can be subjected to an extraction unit operation (not shown) as is well known in the art to remove naphthenes. Suitable solvents for extractive distillation include tetrahydrothiophene 1,1-dioxide (or sulfolane), diethylene glycol, triethylene glycol, or tetraethylene glycol. One advantage of removing naphthenes is to enhance the purity of benzene co-product. The higher boiling fraction from the fractionation is used as feed to the xylene separation unit operations as will be discussed later. Also, fractionation may be used to remove lights, i.e., components having a boiling point less than benzene.

Returning to the toluene and lighter component stream introduced via line 302, it is desirable to recover not only toluene for the transalkylation unit operation and at least a portion of any xylene contained in the lower boiling fraction but also at least some of the benzene as a co-product. As shown, the lower boiling fraction is passed to distillation column 304 to provide a benzene-containing lower boiling fraction which is removed via line 306 and a higher boiling fraction which is removed via line 308. The benzene in line 306 may be used as a co-product, or a portion of the benzene may be used for transalkylation. Where the benzene is a desired product, additional purification steps may be useful depending upon benzene product purity requirements.

The lower boiling fraction in line 308 from distillation column 304 contains toluene and higher boiling components. If desired, the toluene may be subjected to a toluene disproportionation reaction to convert toluene to xylenes and benzene. Whether to use a toluene disproportionation unit operation is dependent upon the feeds and the economics for a given facility. Most frequently little advantage exists in using toluene for disproportionation as opposed to transalkylation due to the increase in production of benzene. FIG. 3 does not depict a toluene disproportionation unit operation.

Disproportionation is effected through a catalytic reaction. The disproportionation catalyst comprises a molecular sieve and a refractory inorganic oxide. The preferred molecular sieves are zeolitic aluminosilicates, or zeolites, which may be any of those which have a $Si:Al_2$ ratio greater than about 10, preferably greater than 20, a pore diameter of about 5 to 8 angstroms. Specific examples of zeolites which can be used are the MFI, MEL, EUO, FER, MFS, MTT, MTW, TON, TWW, MOR and FAU types of zeolites. Pentasil zeolites MFI, MEL, MTW and TON are preferred, and MFI-type zeolites, often designated ZSM-5, are especially preferred.

Preferably the zeolitic aluminosilicate, or zeolite, has an enhanced surface silicon content, i.e., the proportion of silicon at the surface of the zeolite is greater than the proportion in the bulk of the zeolite. The "surface" is defined for purposes of the present invention as a layer at the external surface of the zeolite which is less than about 100 angstroms in depth, and usually about 10 angstroms or less in depth. Optimally the silicon/aluminum ratio is increased by about 5 or more at the surface of the zeolite relative to the ratio in the bulk of the zeolite. The catalysts are usually prepared with a refractory binder or matrix. Suitable binders include inorganic oxides such as one or more of alumina, magnesia, zirconia, chromia, titania, boria, thoria, zinc oxide and silica. A preferred binder or matrix component is a phosphorus-containing alumina (hereinafter referred to as aluminum phosphate). The amount of zeolite present in the bound catalyst can vary considerably but usually is present in an amount from about 30 to 90 mass percent and preferably from about 50 to 80 mass percent of the catalyst. In a preferred embodiment, the catalyst consists essentially of the zeolite and binder.

Advantageous disproportionation catalysts have an X-ray powder diffraction pattern such that the ratio of peak intensities at respective two-$\Theta$ Bragg angle positions of about 48.5: 46.5 is at least about 1.1 and the ratio of peak intensities at respective two-$\Theta$ Bragg angle values of about 48.5:47.5 is at least about 1.0.

The catalyst could contain a metal component, preferably selected from components of the group consisting of gallium, rhenium and bismuth. Preferably, however, the catalyst contains no metal component.

Optionally, the catalyst may be subjected to precoking in order to increase the proportion of paraxylene in the $C_8$ aromatics product. Further details relative to precoking are disclosed in U.S. Pat. No. 4,097,543, incorporated herein by reference.

Conditions employed for disproportionation typically include a temperature of from about 200° to 600° C., and preferably from about 250° to 575° C. The temperature required to maintain the desired degree of conversion will increase as the catalyst gradually loses activity during processing. Normal end-of-run temperatures may therefore exceed start-of-run temperatures by 65° C. or more. The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of para-xylene at the expense of conversion. Weight hourly space velocity generally is the range of from about 0.2 to 10 $hr^{-1}$.

Returning to FIG. 3, the higher boiling fraction in line 308 is directed to toluene distillation column 310 to provide a lower boiling fraction containing toluene which is withdrawn via line 312 and a higher boiling fraction containing xylenes which is withdrawn via line 314.

As shown, the higher boiling fraction from the deheptanizer (not shown) contains xylenes and is provided via line 316 as a portion of the feed to xylene column 318. This stream contains $C_9A$ (alkylaromatic of 9 carbon atoms) and higher. Also fed via line 314 as a portion of the feed to xylene column 318 is the higher boiling fraction from toluene distillation column 310. Since the deheptanizer takes most of the xylenes and higher boiling aromatics to the higher boiling fraction, the composition of the stream in line 302 contains a small fraction of the xylenes in the fresh feed to the deheptanizer. The use of a disproportionation unit operation, of course, would increase the contribution of the xylenes being provided to xylene column 318 via line 314.

As another option, where benzene and toluene are desired as reactants for transalkylation, distillation column 304 may be eliminated, or a significant portion of the benzene may be contained in the higher boiling fraction from distillation column 304 and thus benzene would become a significant component of the lower boiling fraction from toluene distillation column 310.

As shown, xylene column 318 is in association with column 330 whereby an ortho-xylene product can be obtained. In the broader aspects of this invention, ortho-xylene need not be recovered as a separate product and only xylene column 318 need be used. Alternatively, ortho-xylene can be selectively recovered from the overhead from xylene column 318. For purposes of understanding, three options are discussed herein.

In the first option, as shown in FIG. 3, the xylene-containing feed is introduced into xylene column 318 to provide a lower boiling fraction containing para-xylene and meta-xylene which is passed via line 320 to para-xylene separator 322. A higher boiling fraction is withdrawn from xylene column 318 via line 328 and contains ortho-xylene as well as other higher boiling components including $C_9A$. This higher boiling stream is fractionated in ortho-xylene column 330 to provide a lower boiling fraction rich in ortho-xylene which is withdrawn via line 332 and a higher boiling fraction containing $C_9A$ which is withdrawn via line 334.

In the second option, a single xylene column assembly is used and the lower boiling fraction contains all xylene isomers and the higher boiling fraction contains $C_9A$. The para-xylene separator thus separates not only the para isomer from the meta-isomer but also from the ortho isomer. Since only the para-xylene isomer is recovered as product, the meta- and ortho-xylenes will be contained in the non-equilibrium xylene mixture subjected to isomerization.

The third option is that xylene column 318 provides a lower boiling fraction containing all xylene isomers and is subjected to fractionation to selectively remove ortho-xylene as a higher boiling fraction and the lower boiling fraction will contain the para- and meta-isomers and is passed to para-xylene separator 322.

It is also within the scope of this invention that only the ortho-isomer be recovered as product. In such instances, the para- and meta-isomers need not be subjected to para-xylene separation and can be isomerized.

Para-xylene separator 322 can be of any convenient type and design such as a fractional crystallization process or an adsorptive separation process, both of which are well known in the art, and preferably is based on the adsorptive separation process. Such adsorptive separation can recover over 99 mass-percent pure para-xylene which is withdrawn via line 324. At least a portion of any residual toluene in the feed to the separation unit is extracted along with the para-xylene, fractionated out in a finishing column within the unit. Thus, the raffinate from the para-xylene separator 322 is almost entirely depleted of para-xylene, to a level usually of less than 1 mass-percent and is passed via line 326 to reactor 342 which will be described later.

The higher boiling fraction in line 334 from column 318 or 330 depending upon the option selected, contains $C_9A$ and higher molecular weight hydrocarbons. This stream is passed to heavies distillation column 336 to provide a lower boiling fraction containing $C_9A$ which is withdrawn via line 338 and a higher boiling fraction containing hydrocarbons having at least 11 carbon atoms which is withdraw via line 340. The lower boiling fraction in line 338 is directed to reactor 342. Preferably the lower boiling fraction contains a significant portion of the $C_{10}A$ in the feed to heavies distillation column 336 since $C_{10}A$ can, under transalkylation conditions, yield xylenes.

In a further alternative, especially where the catalyst effecting transalkylation is relatively tolerant of higher alkylaromatics, i.e., does not result in undue coking, the higher boiling fraction in line 334 may be passed to reactor 342 without the use of a heavies distillation column. In such a case, a purge stream is withdrawn to prevent an undue build-up of such heavier alkylaromatics.

Reactor 342 is an integrated transalkylation and xylene isomerization reactor system. As used herein, an integrated reactor system is one in which at least an aliquot portion of transalkylation product is passed to a zone in which xylene isomerization is occurring. The reactor system may be sequential, i.e., a defined xylene isomerization zone sequentially follows a defined transalkylation zone, or both the transalkylation and xylene isomerization may occur in the same zone.

Figure 1:
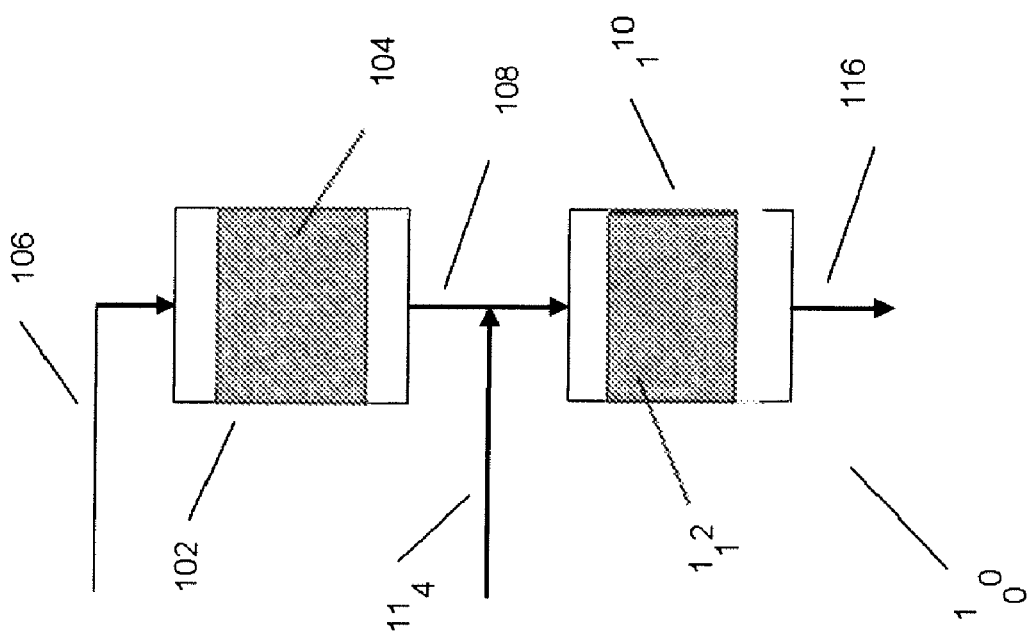
FIG. 1 is a schematic representation of a reactor system having two separate reactor vessels for practicing processes in accordance with this invention.

FIGS. 1 and 2 depict various integrated transalkylation and xylene isomerization reactor systems. The system depicted in FIG. 1 generally designated by 100 involves the use of two reactors in sequential flow sequence. Transalkylation reactor 102 has therein catalyst bed 104. Feed to transalkylation reactor 102 is provided by line 106. While one line is shown, it is contemplated that the feed components can be provided by separate lines and the reaction mixture formed within reactor 102. The feed components provided by line 106 are derived from line 312 which is the toluene-containing lower boiling fraction from toluene column 310 and line 338 which is the $C_9A$-containing lower boiling fraction from heavies column 336. If desired, all or a portion of the non-equilibrium xylene mixture derived from line 326 can be introduced into transalkylation reactor 102 via line 106.

Line 108 is adapted to direct transalkylation product from reactor 102 to xylene isomerization reactor 110. As shown, line 114 is provided to introduce all or a portion of the non-equilibrium xylene mixture derived from line 326 into xylene isomerization reactor 110. Xylene isomerization reactor contains catalyst bed 112. The isomerate can be withdrawn via line 116.

FIG. 2 depicts a reactor system 200 having two zones within a single vessel 202. As shown, vessel 202 contains two distinct catalyst beds, transalkylation catalyst bed 204 and xylene isomerization bed 206. In a preferred embodiment, a single catalyst bed having both activity for transalkylation and activity for xylene isomerization is employed as shown in FIG. 3. Feed to reactor vessel 202 is provided by line 208 and one or both of lines 210 and 210A. While one line is shown, it is contemplated that various feeds can be provided by different lines and mixed within the reactor. The feed components provided by line 208 are derived from line 312 which is the toluene-containing lower boiling fraction from toluene column 310 and line 338 which is the $C_9A$-containing lower boiling fraction from heavies column 336. If desired, all or a portion of the non-equilibrium xylene mixture derived from line 326 can be introduced into reactor 202 via line 210. If desired, all or a portion of the non-equilibrium xylene mixture derived from line 326 can be introduced between catalyst beds 204 and 206 via line 210A. The isomerate can be withdrawn via line 212.

The processes of this invention provide considerable flexibility in the transalkylations that can be effected to generate xylenes. Thus one or both of benzene and toluene can be used as the Light Aromatic and the Heavier Aromatic may be one or both of $C_9A$ and $C_{10}A$ with the result that xylenes are formed directly or through multiple transalkylation steps as are well know such as trimethylbenzene and benzene first forming xylene and toluene and toluene and additional trimethylbenzene forming xylene.

The transalkylation conditions including catalyst can vary widely. The preferred catalyst is a metal stabilized transalkylation catalyst. Such catalyst comprises a zeolite component, a metal component, and an inorganic oxide component. The zeolite component typically is either a pentasil zeolite, which include the structures of MFI, MEL, MTW, MTT and FER (IUPAC Commission on Zeolite Nomenclature) or MWW or a beta zeolite or a mordenite. Preferably it is mordenite zeolite. The metal component typically is a noble metal or base metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Preferably the metal component comprises rhenium. Suitable metal amounts in the transalkylation catalyst range from about 0.01 to about 10 mass-percent, with the range from about 0.1 to about 3 mass-percent being preferred, and the range from about 0.1 to about 1 mass-percent being highly preferred. Suitable zeolite amounts in the catalyst range from about 1 to about 99 mass-percent, preferably between about 10 to about 90 mass-percent, and more preferably between about 25 to about 75 mass-percent. The balance of the catalyst is composed of inorganic oxide binder, preferably alumina. In some instances, it may be desirable to modify the catalyst such as by sulfiding either in-situ or ex-situ. One transalkylation catalyst for use in the present invention is disclosed in U.S. Pat. No. 5,847,256, the teachings of which are incorporated herein by reference.

Conditions employed for transalkylation normally include a temperature of from about 200° to about 540° C. and moderately elevated pressures broadly ranging from about 100 kPa to 10 MPa absolute. The transalkylation reaction can be effected over a wide range of space velocities, with higher space velocities effecting a higher ratio of para-xylene at the expense of conversion. Weight hourly space velocity generally is in the range of from about 0.1 to about 30 hr$^{-1}$. The feedstock is preferably transalkylated in the vapor phase and in the presence of hydrogen. For liquid phase transalkylation, the adding of hydrogen is optional. If present, free hydrogen is associated with the feedstock and recycled hydrocarbons in an amount of about 0.1 moles per mole of alkylaromatics up to about 10 moles per mole of alkylaromatic. This ratio of hydrogen to alkylaromatic is also referred to as hydrogen to hydrocarbon ratio.

Transalkylation of Heavier Aromatics to produce xylenes requires the presence of Light Aromatics, which can be supplied via the lower boiling fraction from toluene column 310 or in whole or part made from the transalkylation of benzene with $C_9A$ or higher molecular weight alkylaromatics such as disclosed in copending U.S. Provisional Patent Application No. 60/695,553, filed Jun. 30, 2005, herein incorporated by reference in its entirety.

Typically the mole ratio of Light Aromatics to Heavier Aromatics fed to transalkylation reactor is at least about 0.01:1, preferably from about 0.01:1 to 10:1, more preferably about 0.1:1 to 2:1. The ratio of Light Aromatics to total aromatics will vary depending upon whether all or a portion of the non-equilibrium xylene mixture is contained in the feed. Generally at least about 40, preferably at least about 70, mass percent of the Heavier Aromatics in the feed to the reactor is consumed.

The xylene isomerization serves to re-equilibrate the non-equilibrium mixture of xylenes. For instance, where para-xylene is the sought product and is removed, additional para-xylene is produced by reestablishing an equilibrium or near-equilibrium distribution of xylene isomers. Any ethylbenzene in the para-xylene separation unit raffinate is either converted to additional xylenes or converted to benzene by dealkylation, depending upon the type of isomerization catalyst used and other conditions. Preferably any conversion of ethylbenzene is by dealkylation to reduce complexities in handling larger quantities of naphthenes that typically are involved in the ethylbenzene conversion to xylenes, in which case, the total naphthenes in the combined feeds to reactor 342 are less than about 1, preferably less than about 0.7, mass percent. Conditions that favor isomerization of ethylbenzene include the presence of hydrogen in a mole ratio to hydrocarbon of at least about 0.1:1, say, 0.5 to 6:1, preferably 1.5:1 to 5:1. Preferably the feed stream contains naphthenes, and more preferably a sufficient concentration of naphthenes is provided in the feed stream to enhance the conversion of ethyl-benzene, e.g., between about 2 and 20 mass-percent naphthenes. Preferably, the isomerization is conducted under at least partially vapor phase conditions. The isomerization section may include a hydrogenation unit operation followed by a dehydrogenation unit operation.

Xylene isomerization involves the use of isomerization catalyst under isomerization conditions. The isomerization catalyst is typically composed of a molecular sieve component, a metal component, and an inorganic oxide component. Selection of the molecular sieve component allows control over the catalyst performance between ethylbenzene isomerization and ethylbenzene dealkylation depending on overall demand for benzene. Consequently, the molecular sieve may be either a zeolitic aluminosilicate or a nonzeolitic molecular sieve. The zeolitic aluminosilicate (or zeolite) component typically is either a pentasil zeolite, which include the structures of MFI, MEL, MTW, MTF and FER (IUPAC Commission on Zeolite Nomenclature), MWW, a beta zeolite, or a mordenite. The non-zeolitic molecular sieve is typically one or more of the AEL framework types, especially SAPO-11, or one or more of the ATO framework types, especially MAPSO-31, according to the "Atlas of Zeolite Structure Types" (Butterworth-Heineman, Boston, Mass., 3rd ed. 1992).

The metal component typically is a noble metal component, and may include an optional base metal modifier component in addition to the noble metal or in place of the noble metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Suitable total metal amounts in the isomerization catalyst range from about 0.01 to about 10 mass-percent, with the range from about 0.1 to about 3 mass-percent preferred. Suitable zeolite amounts in the catalyst range from about 1 to about 99 mass-percent, preferably between about 10 to about 90 mass-percent, and more preferably between about 25 to about 75 mass-percent. The balance of the catalyst is composed of inorganic oxide binder, typically alumina. In some instances, it may be desirable to modify the catalyst such as by sulfiding either in-situ or ex-situ. One isomerization catalyst for use in the present invention is disclosed in U.S. Pat. No. 4,899,012, the teachings of which are incorporated herein by reference.

Typical isomerization conditions include a temperature in the range from about 0° to about 600° C. and a pressure from about 100 kPa to about 6 MPa absolute. The weight hourly hydrocarbon space velocity of the feedstock relative to the volume of catalyst is from about 0.1 to about 30 hr$^{-1}$. The hydrocarbon contacts the catalyst in admixture with a gaseous hydrogen at a hydrogen-to-hydrocarbon mole ratio of from about 0.5:1 to 15:1 or more, and preferably a ratio of from about 0.5 to 10. If liquid phase conditions are used for isomerization, then typically no hydrogen is added.

Advantageously, especially where a single reaction vessel is used, common conditions are used for the transalkylation and xylene isomerization. Typically the common conditions comprise a temperature in the range of about 200° to about 540° C. and moderately elevated pressures broadly ranging from about 100 kPa to 6 MPa absolute. Weight hourly space velocity generally is in the range of from about 0.1 to about 30 hr$^{-1}$. A hydrogen-to-hydrocarbon mole ratio of from about 0.1:1 to 15:1 or more, and preferably a ratio of from about 0.5 to 10.

In the embodiments of this invention where a single catalyst is used for both transalkylation and xylene isomerization, the catalyst is typically composed of a molecular sieve component, a metal component, and an inorganic oxide component. The molecular sieve may be either a zeolitic aluminosilicate or a nonzeolitic molecular sieve. The zeolitic aluminosilicate (or zeolite) component typically is either a pentasil zeolite, which include the structures of MFI, MEL, MTW, MTF and FER (IUPAC Commission on Zeolite Nomenclature), MWW, a beta zeolite, or a mordenite. The non-zeolitic molecular sieve is typically one or more of the AEL framework types, especially SAPO-11, or one or more of the ATO framework types, especially MAPSO-31, according to the "Atlas of Zeolite Structure Types" (Butterworth-Heineman, Boston, Mass., 3rd ed. 1992).

The metal component typically is a noble metal component or base metal, or combination thereof. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Suitable total metal amounts in the catalyst range from about 0.01 to about 10 mass-percent, with the range from about 0.1 to about 3 mass-percent preferred. Suitable zeolite amounts in the catalyst range from about 1 to about 99 mass-percent, preferably between about 10 to about 90 mass-percent, and more preferably between about 25 to about 75 mass-percent. The balance of the catalyst is composed of inorganic oxide binder, typically alumina. In some instances, it may be desirable to modify the catalyst such as by sulfiding either in-situ or ex-situ.

Returning to FIG. 3, the effluent from reactor 342 is directed by line 344 to stripper 348. Stripper 348 provides a higher boiling fraction containing xylenes that is passed via line 352 to xylene column 318. A lower boiling fraction from stripper 348 can be passed via line 350 to benzene column 304 to recover benzene and toluene. As described in paragraphs [0017] and [0024] above, stripper 348 may be operated to provide (i) a benzene-containing fraction depleted in xylenes and toluene 350, (ii) a toluene fraction depleted in xylenes 351, and (iii) a xylene fraction depleted in toluene and benzene 352. Stream 350 is passed to benzene column 304, stream 351 is passed to reactor 342, and stream 352 is passed to xylene column 318. Alternatively, the stripper may either be used only to remove lights or be eliminated with the reactor effluent going directly to benzene column 304.

In a further alternative, a portion of the lower boiling fraction from stripper 348 is returned to reactor 342 via line 354 to supply Light Aromatic for transalkylation.

Figure 4:
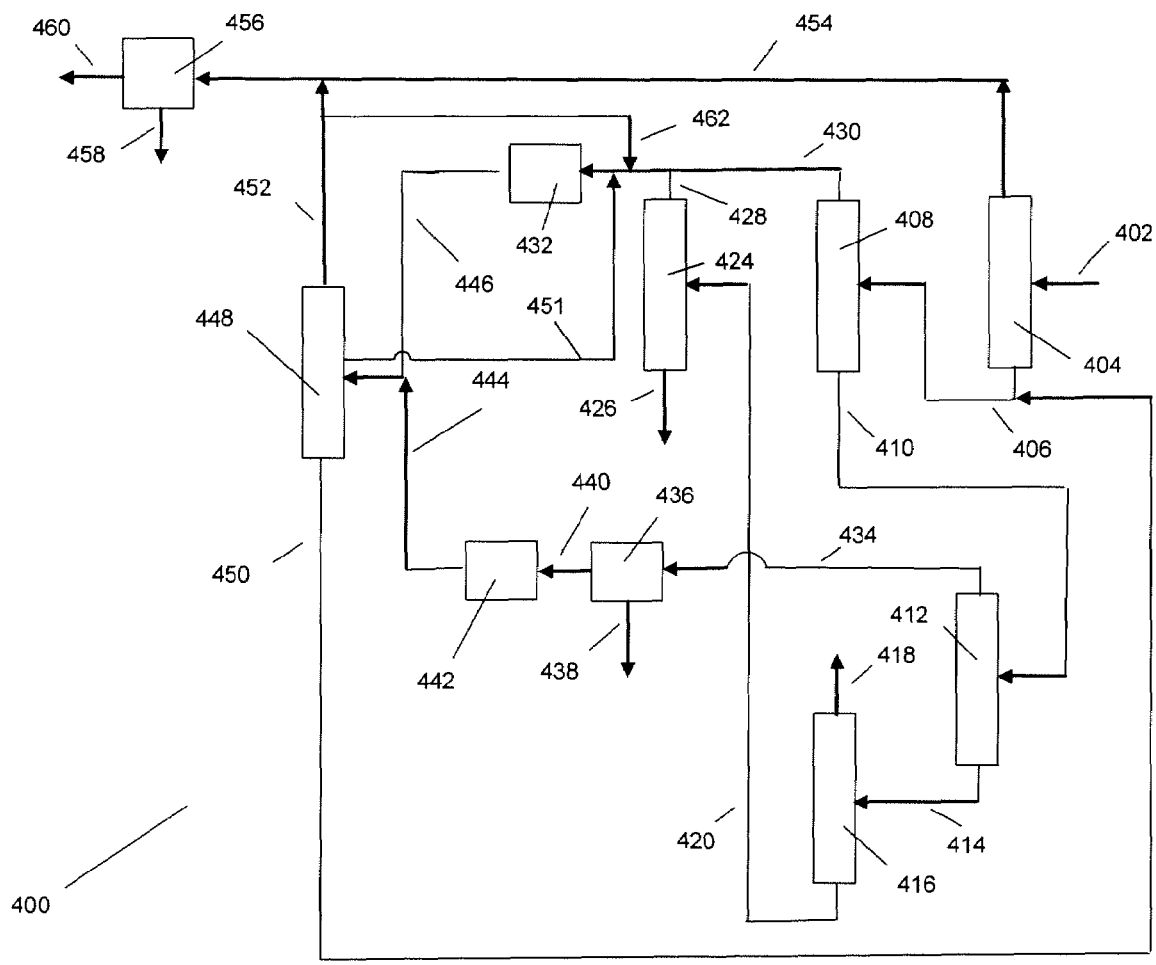
FIG. 4 is a schematic representation of a xylene isomer production apparatus in accordance with this invention.

With respect to FIG. 4, a para-xylene and ortho-xylene production facility, generally designated as 400, is supplied an aromatics-containing feed stream by line 402. The aromatics-containing feed may, for instance, be derived from a reformer. Usually such a stream will have been treated to remove olefinic compounds and lights, e.g., hydrocarbons of four and fewer carbon atoms, removed. It is, however, not essential to the practice of the broad aspects of this invention, to remove any or all of the olefin. The aromatics-containing feed stream contains benzene, toluene and $C_8$ aromatics and typically contains higher aromatics and aliphatic hydrocarbons including naphthenes.

The feed stream is passed to reformate splitter 404 with a bottoms stream containing toluene and higher boiling hydrocarbons being withdrawn via line 406 and fed to toluene column 408. Toluene column 408 provides an overhead containing toluene and a bottoms stream containing $C_8$ and higher aromatics. The bottoms stream is passed via line 410 to xylene column 412. Xylene column 412 provides a bottoms stream containing ortho-xylene and higher boiling compounds including $C_9$ and $C_{10}$ aromatics. This bottoms stream is passed via line 414 to ortho-xylene column 416 where ortho-xylene product is withdrawn as overhead via line 418 and a bottoms stream containing the heavier hydrocarbons is withdrawn via line 420 and passed to heavies column 424. Heavies column 424 provides as an overhead a stream containing $C_9$ and at least some of the $C_{10}$ aromatics with higher boiling compounds, primarily $C_{11}A$ and higher alkyl aromatics, being withdrawn as a bottoms stream via line 426. Alternatively, column 424 may be eliminated as discussed with respect to column 336 of FIG. 3.

The overhead from heavies column 424 is passed via line 428 for combination with the toluene-containing overhead contained in line 430 from toluene column 408. This mixture is fed to transalkylation reactor 432 to produce a transalkylation product containing xylenes.

The overhead provided by xylene column 412 contains para-xylene and meta-xylene and typically ethylbenzene and some of the ortho-xylene and passes through line 434 to para-xylene separation unit 436 which provides a para-xylene product stream that is withdrawn via line 438 and a non-equilibrium mixture of xylene isomers which is passed via line 440 to isomerization reactor 442.

An isomerate is provided by isomerization reactor 442 and is passed via line 444 for combination with the transalkylation product obtained from transalkylation reactor 432 via line 446. The combined streams are provided to stripper 448 where benzene and lighter hydrocarbons are removed as overhead and a bottoms stream containing toluene and heavier hydrocarbons which is withdrawn via line 450 and recycled to toluene column 408.

The overhead of reformate splitter 404 is withdrawn via line 454 and passed to extraction unit 456 as is the overhead withdrawn from stripper 448 via line 452. If desired, a portion of the stream in line 452 may be recycled to reactor 432 via line 462. Extraction unit 456 separates aliphatics from benzene and provides an aliphatic-rich stream that is removed via line 458 and a benzene product stream that is withdrawn via line 460. Alternatively, as described in paragraphs [0017] and [0024] above, stripper 448 may be operated to provide (i) a benzene-containing fraction depleted in xylenes and toluene 452, (ii) a toluene fraction depleted in xylenes 451, and (iii) a xylene fraction depleted in toluene and benzene 450. Stream 452 is passed to extraction unit 456 and stream 451 is passed to reactor 432. Depending upon the amount of toluene in the stream 450, it may be passed to toluene column 408 or it may be passed to xylene column 412 (also shown in FIG. 3 stream 352 being passed to xylene column 318).

Figure 4A:
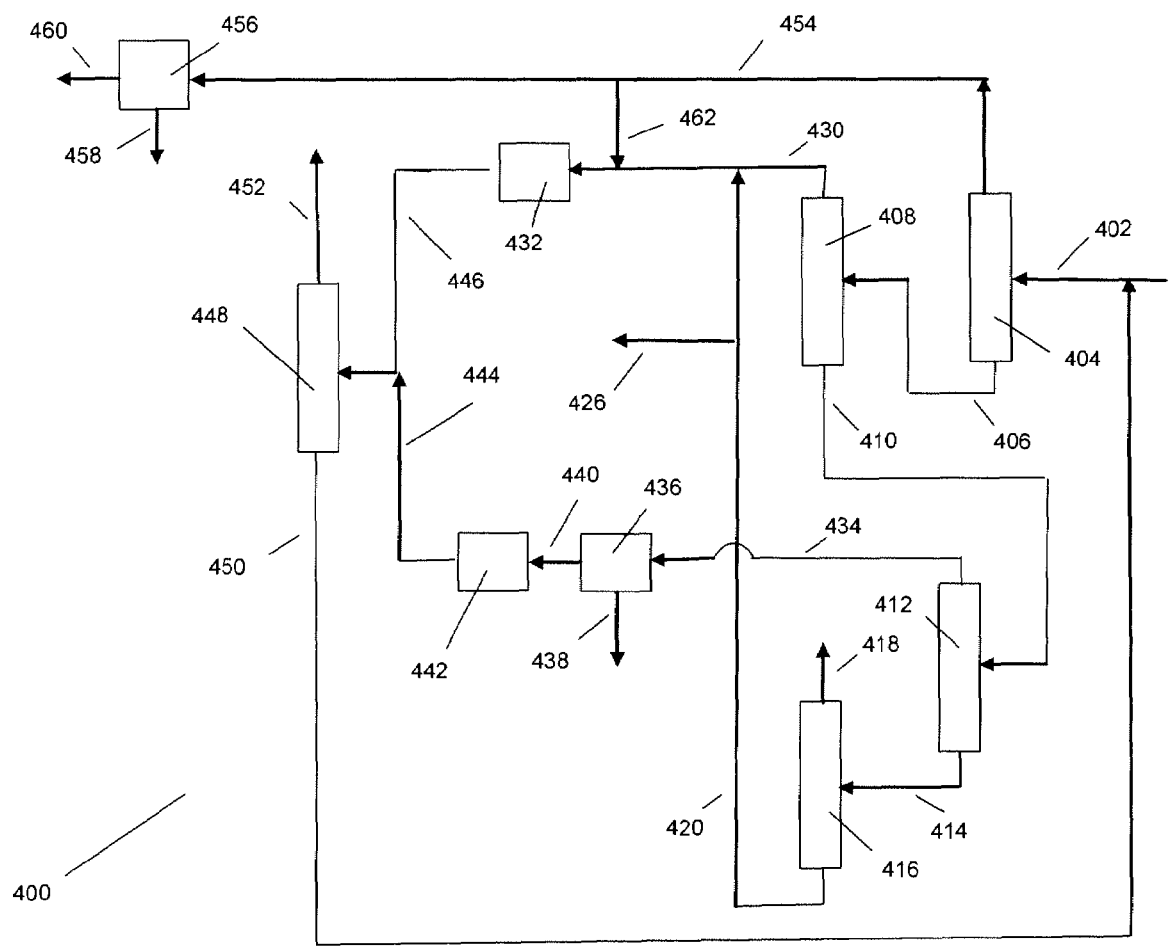
FIG. 4A is a schematic representation of a xylene isomer production apparatus similar to that depicted in FIG. 4.

The apparatus depicted in FIG. 4A is essentially the same as that depicted in FIG. 4 and the same numerical designations are used for the same or similar unit operations. In the apparatus of FIG. 4A, stripper 448 provides an overhead that is primarily lower boilers than benzene, which is exhausted via line 452, and a bottoms stream containing benzene, toluene and xylenes. The bottoms stream is directed via line 450 to benzene column 404. A portion of the overhead in line 454 from benzene column 404 can be recycled to transalkylation reactor 432 via line 462. Additionally, the heavies column is eliminated such that the heavies-containing stream in line 420 is passed to transalkylation reactor 432. A purge is taken via line 426.

What is claimed is:

1. An apparatus for manufacturing xylene isomer comprising:
   a. a toluene distillation assembly having a feed inlet, a first outlet adapted to receive a toluene-containing fraction and a second outlet below said first outlet adapted to receive a xylene-containing fraction;
   b. a xylene distillation assembly having a feed inlet in fluid communication with the second outlet of the toluene distillation assembly, said xylene distillation assembly having a first outlet adapted to receive a para-xylene-containing fraction and a second outlet below said first outlet adapted to receive a $C_9A$-containing fraction;
   c. a selective xylene isomer separation assembly having a feed inlet in fluid communication with the first outlet of the xylene distillation assembly, a product outlet adapted to receive selectively separated xylene isomer, and a reject outlet adapted to receive a non-equilibrium mixture of xylene isomers;
   d. at least one reactor having at least one feed inlet, at least one feed outlet and therebetween catalyst, at least one of said reactors contains catalyst adapted for transalkylation and at least one of said reactors contains catalyst adapted for xylene isomerization, in which the first outlet of the toluene distillation assembly and the second outlet of the xylene distillation assembly are in fluid communication with the at least one reactor containing catalyst adapted for transalkylation and in which the reject outlet of the selective xylene isomer separation assembly is in fluid communication with the at least one reactor containing catalyst adapted for xylene isomerization; wherein one reactor contains a zone having catalyst for transalkylation and subsequent, in fluid flow direction, a zone having catalyst for xylene isomerization, said reactor having at least two feed inlets, in which:
  (i) at least one first feed inlet is prior in fluid flow direction to the zone having catalyst for transalkylation, and each of the first outlet of the toluene distillation assembly and the second outlet of the xylene distillation assembly are in fluid communication with a first feed inlet and
  (ii) at least one second feed inlet is subsequent in fluid flow direction to the zone having catalyst for transalkylation, and the reject outlet of the selective xylene isomer separation assembly is in fluid communication with at least one second feed inlet; and
e. a stripper distillation assembly having an inlet in fluid communication with the feed outlet of the at least one reactor containing catalyst adapted for transalkylation and with the feed outlet of the at least one reactor containing catalyst for xylene isomerization, said stripper distillation assembly having:
  (i) a first outlet adapted to receive a benzene-containing fraction;
  (ii) a second outlet adapted to receive a toluene-containing fraction which outlet is in fluid communication with at least one reactor; and
  (iii) a third outlet adapted to receive a xylene-containing fraction.

2. The apparatus of claim 1 wherein the first outlet adapted to receive a benzene-containing fraction is in fluid communication with an extraction unit.

3. The apparatus of claim 1 wherein the first outlet adapted to receive a benzene-containing fraction is in fluid communication with a benzene distillation assembly.

4. The apparatus of claim 1 wherein the third outlet adapted to receive a xylene-containing fraction is in fluid communication with the xylene distillation assembly.

5. The apparatus of claim 1 wherein the third outlet adapted to receive a xylene-containing fraction is in fluid communication with the toluene distillation assembly.

6. The apparatus of claim 1 wherein the third outlet adapted to receive a xylene-containing fraction is in fluid communication with both the toluene distillation assembly and the xylene distillation assembly.

* * * * *